United States Patent [19]

Holter

[11] Patent Number: 4,883,456
[45] Date of Patent: Nov. 28, 1989

[54] ATTITUDE AND PRESSURE RESPONSIVE VALVE

[76] Inventor: John W. Holter, Valley Forge Circle 1000-619, King of Prussia, Pa. 19405

[21] Appl. No.: 158,695

[22] Filed: Feb. 22, 1988

[51] Int. Cl.⁴ .............................................. A61M 5/00
[52] U.S. Cl. ...................................... 604/9; 604/247; 137/38
[58] Field of Search .................................. 604/9–10, 604/247; 137/38, 513.3, 513.5, 513.7, 848, 849

[56] References Cited

U.S. PATENT DOCUMENTS

| | | | |
|---|---|---|---|
| 1,144,657 | 6/1915 | Keller | 137/513.7 |
| 2,376,123 | 5/1945 | Cohen | 137/848 |
| 2,969,066 | 1/1961 | Holter et al. | 604/9 |
| 3,566,875 | 3/1971 | Stoehr | 604/9 |
| 3,861,415 | 1/1975 | Larsen | 137/513.5 |
| 3,889,687 | 6/1975 | Harris et al. | 604/10 |
| 3,926,375 | 12/1975 | Reeder et al. | 137/513.5 |
| 4,215,695 | 8/1980 | Spitz et al. | 604/9 |
| 4,605,395 | 8/1986 | Rose et al. | 604/9 |
| 4,621,654 | 11/1986 | Holter | 137/38 |
| 4,675,003 | 6/1987 | Hooven | 604/9 |
| 4,694,651 | 9/1987 | Yardley et al. | 137/513.5 |

Primary Examiner—C. Fred Rosenbaum
Assistant Examiner—Kathleen A. Dabey
Attorney, Agent, or Firm—Richard D. Weber

[57] ABSTRACT

A pressure and attitude responsive valve comprises a resilient substantially cylindrical hollow valve body having an opening in one end to receive a pressurized fluid to be regulated. The opposite valve body end is closed by a frusto-conical end wall having a central opening therein. A valve ball, larger than the opening but smaller than the valve body bore, is disposed within the valve body to open or close the opening depending on the attitude of the valve body. Longitudinal slits in the wall of the valve body permit resilient deformation of the wall and an opening of the slits upon occurrence of a predetermined pressure gradient. The valve is disposed in a valve housing in series with a check valve to comprise a shunt valve assembly for treatment of hydrocephalus.

5 Claims, 2 Drawing Sheets

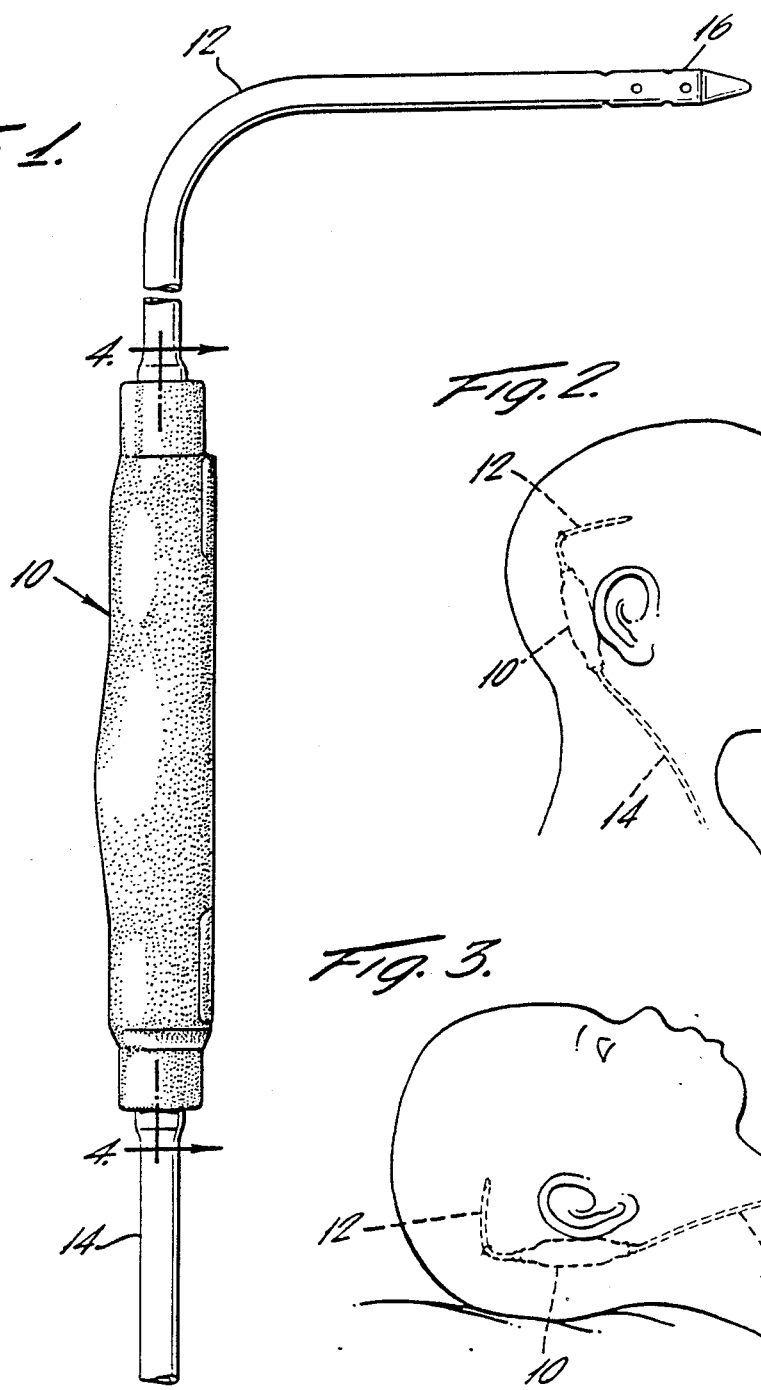

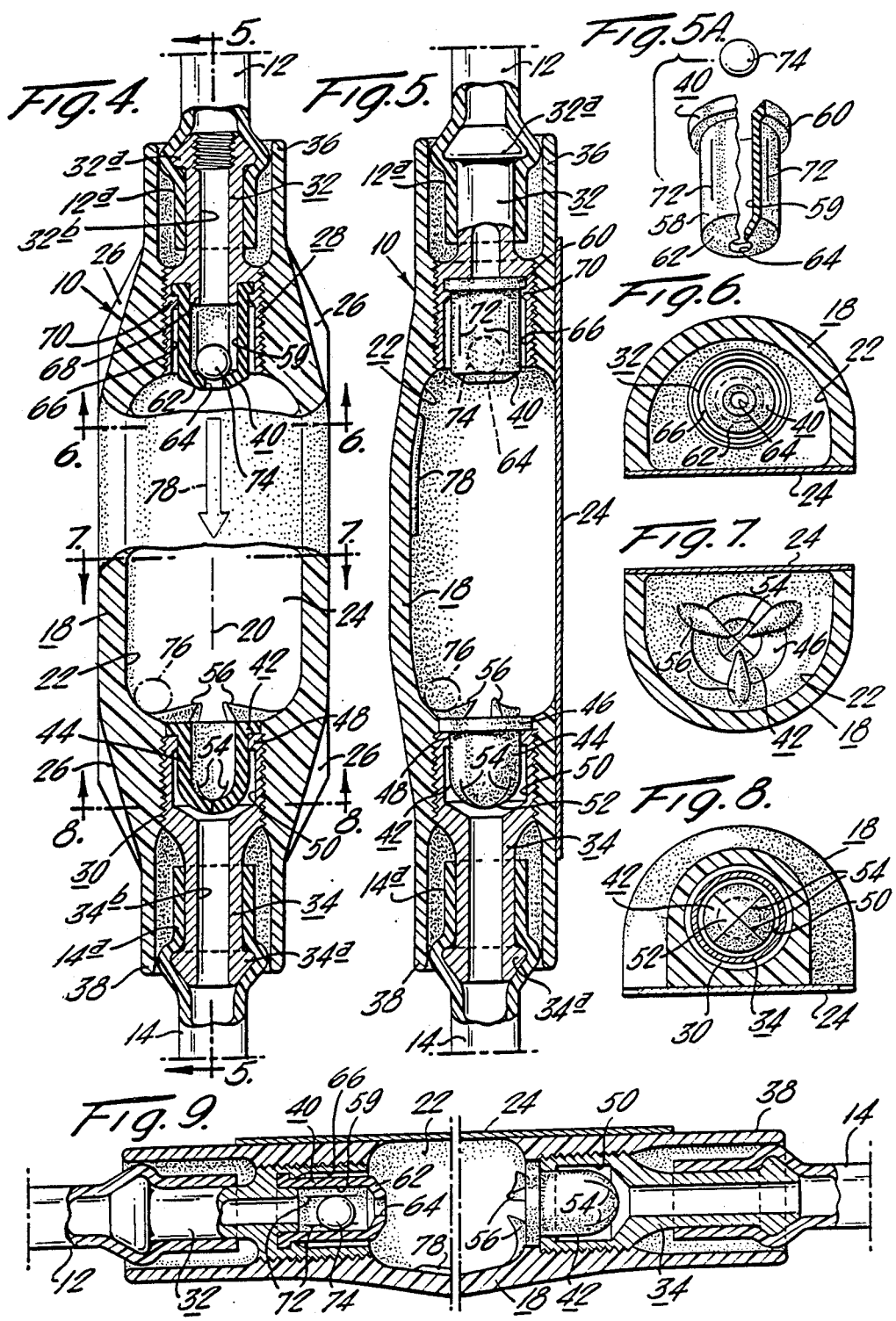

ATTITUDE AND PRESSURE RESPONSIVE VALVE

BACKGROUND OF THE INVENTION

The present invention relates generally to a valve for providing pressure relief in response both to attitude and pressure conditions, and relates more particularly to such a valve adapted for implantation to relieve intracraneal pressure in treatment of hydrocephalus.

Devices for draining ventricular fluid in cases of hydrocephalus have been available for some time. An early example of such a device is shown in my U.S. Pat. No. 2,969,066, issued Jan. 24, 1961. These devices essentially are pressure responsive valves which open upon the occurrence of a predetermined gradient across the valve to allow flow of cerebrospinal fluid sufficient to lower the ventricular pressure to the desired level.

Existing shunt valves consisting of the single pressure differential type cannot accommodate the great variation of pressure occurring when a patient changes position from horizontal to vertical.

A solution to this problem is provided by the valve assembly shown in my U.S. Pat. No. 4,621,654, issued Nov. 11, 1986 and in which the valve assembly is responsive both to attitude and pressure. A pressure responsive valve and an attitude responsive valve are disposed in a parallel arrangement which provides an alternate flow path dependent upon the patient's attitude. The pressure responsive valve opens under a relatively high pressure gradient, while the attitude responsive valve opens when the patient is in a substantially horizontal position.

Although the valve disclosed in U.S. Pat. No. 4,621,654 would accomplish its intended purpose, it suffers the disadvantages of being complex in design, requiring a relatively large number of parts and hence being expensive to manufacture. It is also somewhat bulky in size, a distinct disadvantage considering the region of implantation.

The present device due to its novel structure, can be more compact, thereby reducing the likelihood of implant complications such as erosion through the skin, a frequent problem with this type of device. The present valve assembly further comprises a fewer number of pieces then the valve assembly of U.S. Pat. No. 4,621,654 and accordingly is less expensive to manufacture and assemble. In addition, the present valve assembly is more readily made of plastic elements, tending to minimize the interference of the implanted valve with X-ray scanning techniques such as computed tomography.

SUMMARY OF THE INVENTION

In the present invention, a compact valve responsive to both attitude and pressure is provided in the fluid flow path. This valve comprises a hollow, generally cylindrical valve body into one open end of which the fluid is introduced. The valve is oriented in the valve assembly such that upon implantation, the open end of the valve body is directed upwardly when the patient is in an upright position. The opposite end of the valve body includes a small opening which in the vertical attitude of the valve assembly is closed by a valve ball larger than the opening. One or more slits are provided in the valve body, which slits open upon occurrence of a predetermined pressure gradient.

When the patient is erect, such as when standing or seated, the ball closes the opening, and the ventricle pressure is controlled by the valve body slits which open upon occurrence of a relatively high pressure gradient. When the patient lies down, the ball rolls away from the opening, permitting pressure relief even under low pressure gradient conditions. The valve assembly in addition to the novel valve described, also includes a low pressure check valve in the fluid flow path to prevent the possibility of any reverse fluid flow. The described valves are disposed within a hollow valve housing and preferably including a pumping chamber between the valves to permit the testing of the operability of the assembly.

It is accordingly a first object of the invention to provide a shunt valve for treatment of hydrocephalus which is both pressure responsive and attitude responsive to provide relief of intracraneal pressure regardless of the attitude of the patient and the length of the catheter into which the valve discharges.

A further object of the invention is to provide a valve as described of a relatively simple construction which can readily be miniaturized, and which can be fabricated of materials suitable for implantation.

Another object of the invention is to provide a valve as described which is comprised of relatively few parts, thereby simplifying manufacture and assembly and permitting manufacture at a relatively low cost.

Still another object of the invention is to provide a valve as described having only a few, very small radioluscent or metal parts and accordingly minimizing interference with X-ray scanning procedures.

Additional objects and advantages of the invention will be more readily apparent from the following description of a preferred embodiment thereof.

BRIEF DESCRIPTION OF THE DRAWINGS

FIG. 1 is a side elevational view of a valve assembly in accordance with the invention connected at its upper end with a ventricle catheter and at its lower end to a partially illustrated peritoneal catheter;

FIG. 2 is a schematic elevational view showing the assembly of FIG. 1 implanted in a patient's head;

FIG. 3 is a view similar to FIG. 2, but showing the patient in a reclining position;

FIG. 4 is an enlarged sectional view taken along line 4—4 of FIG. 1 and showing interior details of the valve assembly;

FIG. 5 is a sectional view taken along line 5—5 of FIG. 4;

FIG. 5A is an enlarged exploded perspective view of the attitude and pressure responsive valve components;

FIG. 6 is a sectional view taken along line 6—6 of FIG. 4;

FIG. 7 is a sectional view taken along line 7—7 of FIG. 4;

FIG. 8 is a sectional view taken along line 8—8 of FIG. 4; and

FIG. 9 is a reduced sectional view similar to FIG. 4 showing the valve assembly in the horizontal position.

DESCRIPTION OF THE PREFERRED EMBODIMENT

Referring to the drawings and particularly FIGS. 1-3 thereof, a valve assembly 10 in accordance with the present invention is shown connected at its upper end with a ventricular catheter 12 and at its lower end with a peritoneal catheter 14. The valve assembly and attached catheters are adapted for placement beneath the skin of a hydrocephalitic patient in the position generally shown in FIG. 2 with the perforated distal end 16 of the ventricle catheter being appropriately located in a region of accumulated cerebrospinal fluid to provide fluid pressure relief as required. The fluid drained by the ventricle catheter 12 as regulated by the valve assembly 10 passes through the catheter 14 preferably into the peritoneal cavity of the patient. Although the valve assembly is conventionally placed behind the mastoid prominence as illustrated, when used with a peritoneal catheter it may alternately be located in the chest region. This latter location minimizes the risk of infection in the brain area, especially should complications arise requiring a repositioning, reattachment or replacement of the assembly.

Since valve assemblies for relieving ventricular pressure are typically of the type opening in response to the relative pressure between the ventricular catheter and the peritoneal or venous catheter, a markedly different relief function is provided when the patient's position changes from an upright to a reclining attitude due to a change in pressure at the outlet end of the valve assembly. For example, in FIG. 2 with the patient's upper body in an upright position such as when sitting or standing, the pressure at the outer valve pressure will be relatively low since the fluid column within the lower catheter will be in an essentially vertical attitude. In contrast, when the patient is in a reclining position as in FIG. 3, the pressure at the valve outlet will be significantly higher since the fluid in the lower catheter will be substantially horizontal.

As a result, since the valve assembly components are normally selected to effect the desired pressure relief function when the patient is in the upright position of FIG. 2, the desired relief function cannot be obtained when the patient is in the reclining position of FIG. 3 since the downstream catheter pressure will be substantially higher. The conventional type of valve would accordingly permit excessive ventricle pressure buildup when the patient is in the reclining position. If the valve were chosen to provide the appropriate pressure responsive opening when the patient were in the reclining position of FIG. 3, such a valve would produce excessive fluid drainage in the upright position of FIG. 2 with potentially serious results.

The present valve assembly 10 overcomes this shortcoming of conventional pressure responsive valves by incorporating therewithin a novel attitude and pressure responsive valve which will open also when the patient is in a reclining position, thus providing appropriate pressure relief regardless of the patient's position.

The present valve assembly 10 is shown in detail in FIGS. 4–9 and includes a resilient elongated valve housing 18 having a longitudinal axis 20. The housing 18 is hollow, with the walls thereof defining a fluid chamber 22 extending most of the length of the housing. Both the housing 18 and the fluid chamber 22 as shown in FIG. 6 are in section of a D-shape, one wall 24 of the housing being essentially planar and preferably incorporating therewithin a fabric reinforcement layer. The wall 24 projects beyond the housing near the four corners of the housing to form ear portions 26 which facilitate the anchoring of the valve assembly in place such as by means of ligatures.

In order to permit fluid passage into and out of the fluid chamber 22, inlet and outlet openings 28 and 30 respectively are provided at opposite ends of the chamber in alignment with the housing axis 20. Knurled or abraded hollow tubing connectors 32 and 34 are respectively bonded within the openings 28 and 30 and terminate outwardly in enlarged tip portions 32a and 34a. The proximal end 12a of the ventricular catheter 12 is disposed around the outer end of the connector 32 to permit introduction of fluid into the fluid chamber 22 by passage through the central bore 32b of the tubing connector 32. Similarly, the proximal end 14a of the peritoneal catheter 14 is disposed over the outwardly extending ends of the tubing connector 34 to permit passage of fluid from the chamber 22 into the peritoneal catheter by means of the central bore 34b of the connector 34. The tubing connectors 32 and 34 are preferably made of type 316 stainless steel or other suitable metal or plastic. The housing 22 preferably includes integral collar portions 36 and 38 which respectively extend in spaced relation around the connectors 32 and 34 to protect the attachment of the catheter ends.

The flow of fluid through the chamber 22 is governed by a pressure and attitude responsive valve 40 disposed adjacent the tubing connector 32, and a normally closed pressure responsive valve 42 disposed adjacent the tubing connector 34. The order of placement of the valves 40 and 42 within the fluid flow path is not important.

The check valve 42 is responsive to low pressure gradients, for example 5–20 mm $H_2O$ and may be of any suitable type for the purpose. In the illustrated embodiment, the valve 42 comprises a generally cylindrical hollow valve body 44 having an outwardly extending annular flange 46 at its inner end which is seated against the flange 48 of the tubing connector 34. The tubing connector 34 includes an enlarged bore forming valve chamber 50 into which the valve body 44 extends. The outer end of the valve body 44 terminates in a hemispherical shaped end 52 into which a pair of substantially perpendicular slits 54 are cut. Upon occurrence of a predetermined pressure gradient between the interior of the valve body 44 and the chamber 50, the valve body segments formed by the slits 54 will deform outwardly to open the slits and permit a fluid flow from the chamber 22 into the catheter 14. The valve body 44 is held in position between a plurality of integrally molded projections 56 of the housing 18 and the annular flange 48 of the connector 34. The projections 56, which as shown in FIG. 7 total three in number, provide an additional function as described below.

The valve assembly as described thus far is not dissimilar from that disclosed in my U.S. Pat. No. 4,621,654 referred to above. The principal differences resides in the novel attitude and pressure responsive valve 40 which will now be described. This valve 40 replaces the separate, parallel pressure valve and attitude valve of my patent.

Referring to FIGS. 4, 5 and 5A of the drawings, the valve 40 comprises a resilient, substantially cylindrical hollow valve body 58 having an outwardly extending annular flange 60 adjacent the open end thereof. The opposite closed end 62 of the valve body 58 is formed in a frusto-conical configuration with the apex thereof directed into the chamber 22. An orifice 64 is concentrically disposed in the frusto-conical end wall 62 of the valve body 58.

The valve body is secured within an enlarged bore forming a valve chamber 66 within the lower end of the tubing connector 32 by adhesive bonding of the flanged end to the connector. A narrow annular portion 68 of the connector 32 extends partway into the hollow valve body 58, providing an additional adhesive contact area.

In addition, an annular rib 70 of the connector 32 is disposed beneath the flange 60 to further secure the valve body in place.

The valve body 58 comprises a plurality of longitudinal slits 72 which permit the side walls of the valve body to deform outwardly upon the occurrence of a certain pressure gradient between the fluid in the interior of the valve body and the fluid within the chamber 22, thus opening the slits to permit fluid flow therethrough. This pressure responsive aspect of the valve 40 is designed to open when the pressure differential is relatively high, for example, 180 mm $H_2O$.

A ball 74 is disposed within the valve body 58 and cooperates with the frusto-conical end wall 62 and the orifice 64 to open and close the orifice depending upon the attitude of the valve body. The ball 74, which is larger in diameter than the orifice 64 but smaller in diameter than the valve body bore 59, seats by gravity on the frusto-conical valve body end 62 when the valve body is in a substantially vertical position such as shown in FIG. 4, thereby closing the orifice 64. When the valve is disposed in a substantially horizontal position, such as that shown in FIG. 9, the ball due to gravitational force, moves downwardly away from the orifice 64, permitting fluid to flow through the orifice. The ball is larger than the bore 32b of the tubing connector and hence cannot escape from the tubing connector.

To ensure the ball movement away from the orifice under any pressure gradient below that triggering the opening of the pressure responsive valve slit 72, the ball 74 is preferably made of heavy metal such as stainless steel. It may be advantageous to employ a precious metal such as gold to maximize the ball weight and hence the gravity force serving to move the ball away from the orifice when the valve is in a substantially horizontal attitude.

In the highly unlikely event that the ball 74 should become dislodged from the valve body 58, for example due to failure of the body wall, the ball will drop into the chamber 22, creating a potential hazard by threatening to block the check valve 42. The projections 56 prevent such blockage by directing the ball away from the valve as shown in the broken line ball position 76 in FIGS. 4 and 5. Even if the ball were to lodge directly over the projections, fluid flow would continue between the projections.

To minimize the possibility that the valve may accidently be implanted in an inverted attitude, an arrow 78 is molded into the valve housing 18 for reference by the surgeon.

The operation of the valve assembly is automatic and provides a predetermined pressure relief to the cranial ventricles regardless of the patient's attitude. As indicated above, the valve assembly is implanted so as to be in a substantially vertical attitude when the patent is in an upright position, as shown in FIG. 2. The perforated distal end 16 of the ventricle catheter is located in the appropriate cavity to drain the cerebrospinal fluid as required to maintain the desired fluid pressure. The peritoneal catheter 14 is similarly implanted in a well known manner to provide a flow path of drained fluid to the peritoneal region.

Since the entire fluid drainage system including the ventricle catheter 12, the valve assembly 10 and the peritoneal catheter 14 is at all times filled with fluid, it forms a fluid column of substantial length which in the absence of appropriate valve resistance, could reduce the ventricle pressure to an undesireably low pressure. Accordingly, the high pressure responsive valve slits 72 note a substantial pressure differential resistance and will normally operate only when the patient is in the substantially upright position, at which position the pressure at the upper end of the catheter 14 is minimized and the pressure differential across the valve is greatest.

When the patient assumes a horizontal position, the ball 74 as illustrated in FIG. 9 falls away from the opening 64, thereby opening a flow path through the valve body 58. The opening of either the slits 72 or the valve ball 74 will normally raise the pressure in chamber 22 sufficiently to simultaneously open the check valve 40 and permit a fluid flow into the catheter 14.

The chamber 22 may be utilized as a pumping chamber to test the operability of the valves in the manner described in the above-mentioned U.S. Pat. No. 2,969,066. Since the implantation is just beneath the skin, this portion of the chamber may be manually compressed to force fluid within the chamber through the outlet valve.

The elastic portions of the valve assembly including the valve housing 18 and the elastic valve bodies 44 and 58 are preferably made of a rubber like material such as a silicone elastomer or other elastomeric polymer suitable for implantation.

Manifestly, changes in details of construction can be effected by those skilled in the art without departing from the invention.

I claim:

1. A pressure and attitude responsive valve comprising;
   a resilient hollow valve body,
   an inlet opening in one end of said valve body for introduction thereinto of a pressurized fluid to be regulated,
   a circular outlet opening in the opposite end of said valve body,
   a ball larger in diameter than said outlet opening disposed within said valve body and adapted to open or close said outlet opening in accordance with the attitude of said valve body, and
   at least one slit in said valve body adapted to open to permit fluid flow therethrough outwardly from said valve body upon occurrence of a predetermined pressure gradient across the valve body.

2. A pressure and attitude responsive valve comprising;
   a resilient substantially cylindrical hollow valve body,
   an inlet opening in one end of said valve body for introduction thereinto of a pressurized fluid to be regulated,
   the opposite end of said valve body having a frusto-conical configuration and including a concentric outlet opening therein,
   a ball larger than said outlet opening disposed within said valve body and cooperating with said frusto-conical valve body end to open or close said outlet opening in accordance with the attitude of said valve body, and
   at least one longitudinal slit in the cylindrical wall of said valve body adapted to open to permit fluid flow therethrough outwardly from said valve body upon occurrence of a predetermined pressure gradient across the valve body.

3. A shunt valve for draining cerebrospinal fluid comprising;

and elastomeric elongated hollow valve housing defining a fluid chamber therewithin, an inlet port at one end of said housing, means on said housing for connecting said inlet port with a ventricular catheter, and outlet port at the opposite end of said housing, means on said housing for connecting said outlet port with a drainage catheter, said inlet port, chamber and outlet port comprising a fluid flow path, a pressure and attitude responsive valve for regulating fluid flow through said fluid path disposed at one end of said chamber, said pressure and attitude responsive valve comprising a resilient hollow valve body having a substantially cylindrical side wall, one end of said valve body being open to receive the pressurized fluid, a circular outlet opening in the other end of said valve body, a ball larger than said outlet opening disposed within said valve body and being adapted to open or close said outlet opening in accordance with the attitude of said valve body, and at least one slit in said valve body side wall adapted to open to permit fluid flow therethrough outwardly from said valve body upon occurrence of a predetermined pressure gradient across the valve body, said ball being rollingly disposed within said cylindrical valve body side wall adjacent said slit, a check valve in said fluid path at the opposite end of said chamber from said pressure and attitude responsive valve, said check valve requiring a substantially smaller pressure gradient for opening than the slit of said pressure and attitude responsive valve.

4. The invention as claimed in claim 3, wherein said pressure and attitude responsive valve is longitudinally spaced from said check valve in said housing to provide a chamber portion of sufficient size to permit manual compression thereof when implanted in a patient to permit testing of the operability of the shunt valve.

5. The invention as claimed in claim 3, wherein said other end of said valve body includes a frusto-conical configuration concentric with said outlet opening.

* * * * *